US006716244B2

(12) United States Patent
Klaco

(10) Patent No.: US 6,716,244 B2
(45) Date of Patent: Apr. 6, 2004

(54) SEWING CUFF ASSEMBLY FOR HEART VALVES

(75) Inventor: Tammi Klaco, Austin, TX (US)

(73) Assignee: Carbomedics, Inc., Austin, TX (US)

( * ) Notice: Subject to any disclaimer, the term of this patent is extended or adjusted under 35 U.S.C. 154(b) by 0 days.

(21) Appl. No.: 09/745,233

(22) Filed: Dec. 21, 2000

(65) Prior Publication Data

US 2002/0183834 A1 Dec. 5, 2002

(51) Int. Cl.⁷ .................................................. A61F 2/24
(52) U.S. Cl. ...................................... 623/2.4; 623/2.41
(58) Field of Search ............................ 623/2.38–2.41

(56) References Cited

U.S. PATENT DOCUMENTS

| 3,491,376 A | | 1/1970 | Shiley ................................. 3/1 |
| 3,587,115 A | | 6/1971 | Shiley ................................. 3/1 |
| 3,824,629 A | | 7/1974 | Shiley ................................. 3/1 |
| 4,363,142 A | | 12/1982 | Meyer ............................. 3/1.5 |
| 4,510,628 A | | 4/1985 | Kolff ................................. 3/1.5 |
| 4,535,483 A | | 8/1985 | Klawitter et al. ............... 623/2 |
| 4,743,253 A | | 5/1988 | Magladry ....................... 623/2 |
| 4,863,460 A | | 9/1989 | Magladry ....................... 623/2 |
| 5,071,431 A | | 12/1991 | Sauter et al. .................. 623/2 |
| 5,123,919 A | | 6/1992 | Sauter et al. .................. 623/2 |
| 5,178,633 A | * | 1/1993 | Peters ........................ 623/2.38 |
| 5,397,346 A | * | 3/1995 | Walker et al. .............. 623/2.38 |
| 5,397,348 A | | 3/1995 | Campbell et al. ............... 623/2 |
| 5,755,783 A | | 5/1998 | Stobie et al. .................... 623/2 |
| 5,843,179 A | * | 12/1998 | Vanney et al. .............. 623/2.36 |
| 5,855,603 A | * | 1/1999 | Reif ........................... 623/2.38 |
| 5,876,436 A | | 3/1999 | Vanney et al. ................. 623/2 |
| 5,891,195 A | | 4/1999 | Klostermeyer et al. ........ 623/2 |
| 5,910,170 A | | 6/1999 | Reimink et al. ................ 623/2 |
| 5,948,019 A | * | 9/1999 | Shu et al. .................... 623/2.36 |
| 5,957,976 A | * | 9/1999 | Vanney et al. .............. 623/2.38 |
| 6,241,765 B1 | * | 6/2001 | Griffin et al. ............... 623/2.38 |
| 6,358,278 B1 | | 3/2002 | Brendzel et al. ........... 623/2.39 |

FOREIGN PATENT DOCUMENTS

| EP | 0119357 | 9/1984 |
| GB | 1160008 | 7/1969 |
| WO | WO 01/03612 A1 | 1/2001 |

* cited by examiner

*Primary Examiner*—David H. Willse
*Assistant Examiner*—Suzette J. Jackson
(74) *Attorney, Agent, or Firm*—William, Morgan and Amerson, P.C.

(57) ABSTRACT

The present invention provides a prosthetic valve and a sewing cuff assembly for attaching the prosthetic valve in a patient's heart. The suture cuff generally includes at least one lock ring and sewing cuff material disposed at least partially around the lock ring. The valve body includes a peripheral groove for receiving the lock ring therein and securing the lock ring thereto. A stiffening ring may be coupled to the peripheral groove or otherwise provided on the valve body.

23 Claims, 3 Drawing Sheets

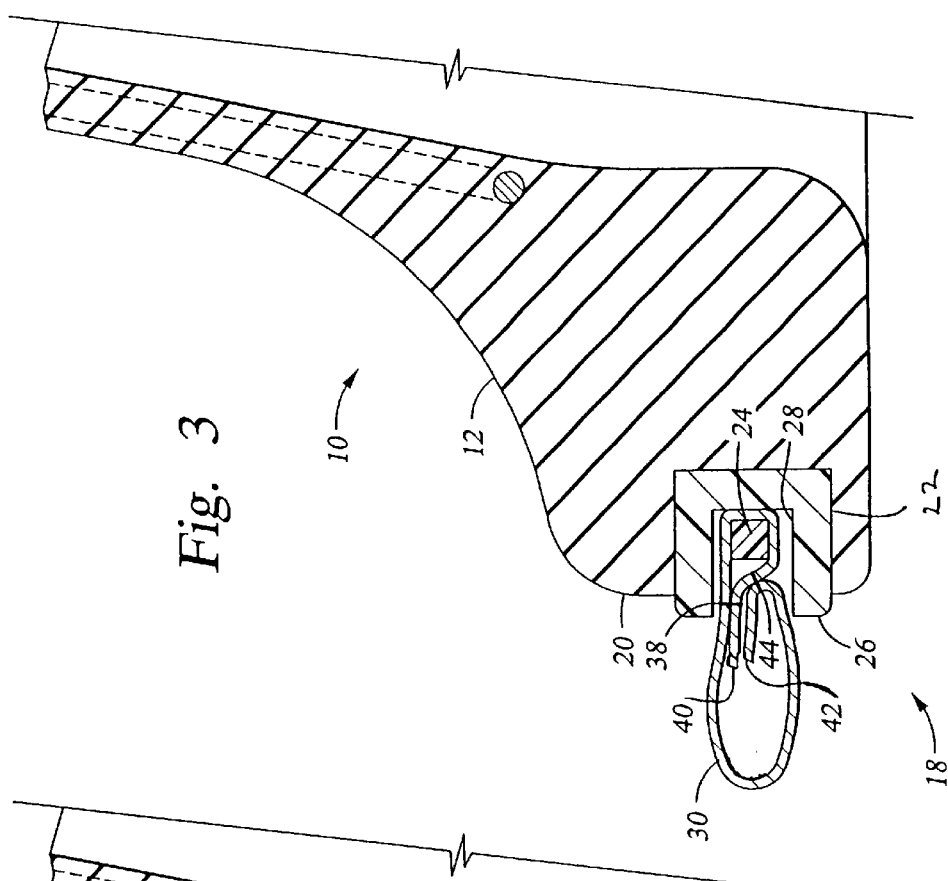
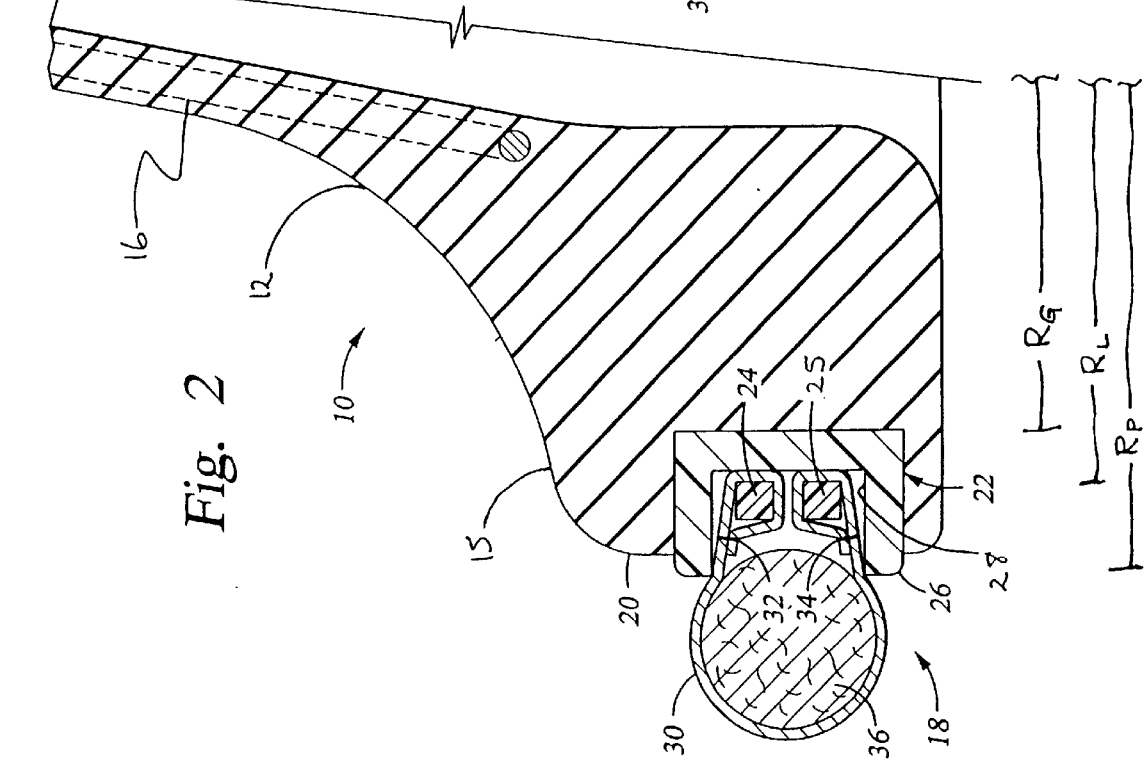

SEWING CUFF ASSEMBLY FOR HEART VALVES

FIELD OF THE INVENTION

The present invention relates to the field of prosthetic heart valves and more particularly to a valve having a sewing cuff assembly that may be easily and securely coupled to the valve for implantation in an annulus of a human heart. In addition, the invention relates to a method for attaching a sewing cuff to a prosthetic heart valve.

BACKGROUND OF THE RELATED ART

Prosthetic heart valves are used to replace diseased heart valves in humans. Prosthetic heart valves include mechanical heart valves, bioprosthetic valves using biological tissue, and polymer valves. The term "mechanical valve" as used herein refers to bi-leaflet heart valves comprising a valve orifice fabricated at least in part of a rigid, biologically compatible material such as pyrolytic carbon, and comprising essentially no biological components. The term "bioprosthetic valve" refers to a bi-leaflet or tri-leaflet heart valve comprising at least some biological components such as tissue or tissue components. The biological components of tissue valves are obtained from a donor animal (typically bovine or porcine), and the valve may comprise either biological materials alone or biological materials with man-made supports or stents. The term "polymeric valve" refers to a tri-leaflet or bi-leaflet heart valve comprising at least some elastomeric polymer components, including at least elastomeric polymer valve leaflets.

Conventional prosthetic heart valves, whether mechanical, bioprosthetic, or polymer valves, typically include an annular valve body comprising an orifice for blood flow through the valve. The valve body can be made of materials such as biocompatible pyrolitic carbon (mechanical valves), porcine or bovine pericardium tissue (bioprosthetic valves), or silicone or polyurethane (polymer valves). Leaflets are coupled to the annular body for movement between an open position and a closed position to allow or prevent blood flow through the orifice. Heart valves may include one, two or three leaflets. The leaflets can he made of pyrolytic carbon, treated tissue, or polymers. The valve is typically attached to a human heart with sutures via a sewing cuff, or some other mechanical attachment means (e.g., staples).

Sewing cuffs generally comprise a toroidal member that is attached to the periphery of the annular valve body to form a site for anchoring sutures to the annulus of the heart during implantation of the heart valve. Sewing cuffs are typically covered with a cloth material, such as polyester, and may also comprise a filler material such as Teflon felt or Dacron cloth. The sewing cuff may be coupled to a peripheral groove on the lower end of the valve body by circumferential cinch-like sutures, or may be mechanically captured adjacent to a stiffening ring, as in U.S. Pat. Nos. 5,397,346 and 5,397,348, hereby incorporated by reference herein.

Existing methods of coupling the sewing cuff to the valve body involve prolonged and repeated handling of the heart valve body. Because attachment of the sewing cuff to the heart valve is a relatively labor-intensive and expensive part of valve fabrication, and because heart valves are more susceptible to damage the more they are handling during assembly, packaging and storage, there is a need for a sewing ring that can be quickly and securely coupled to the valve body with minimal handling.

Another problem associated with prosthetic heart valves is the size and configuration of the suture cuff used to attach the heart valve in the body. It is desirable to maximize the flow area (i.e. the orifice) of the valve. Accordingly, the radial thickness added by the sewing ring is desirably kept to a minimum. Currently, some replacement heart valve designs have large or bulky sewing cuffs, thereby reducing the area available for blood flow. These designs may include additional material located on the outer diameter of the base of the replacement valve. The added bulk of the sewing cuff also makes the valve less flexible, thus making conformation to natural anatomy more difficult.

Therefore, there is a need for a heart valve and sewing cuff which can be assembled together with a minimum of handling, and a method for rapidly and securely affixing a sewing cuff to a heart valve. The assembled valve preferably minimizes the radial thickness of the sewing cuff assembly and maximizes the blood flow orifice area.

SUMMARY OF THE INVENTION

The present invention generally provides a sewing cuff assembly and a heart valve to which the sewing cuff assembly is coupled. The invention further provides a method for attaching a sewing cuff assembly to a heart valve and attaching the assembled heart valve and sewing cuff assembly in a human heart.

In one aspect, embodiments of the invention provide a heart valve comprising a valve body having an outer circumferential rim and a suture cuff assembly comprising at least one lock ring and a material disposed at least partially around and secured to the lock ring. The suture ring may include a filler material disposed inside at least a portion of the material disposed around the lock ring.

In another aspect, a sewing ring for a heart valve is provided comprising at least a pair of lock rings and an attachment material disposed at least partially around the pair of lock rings. A filler material may be disposed at least partially between the attachment material and the lock rings.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 2 is a partial cross sectional view of a valve body having one embodiment of a suture cuff assembly attached thereto.

FIG. 3 is a cross sectional view of another embodiment of a lock ring and suture cuff assembly.

DETAILED DESCRIPTION OF THE PREFERRED EMBODIMENT

Figure 1:
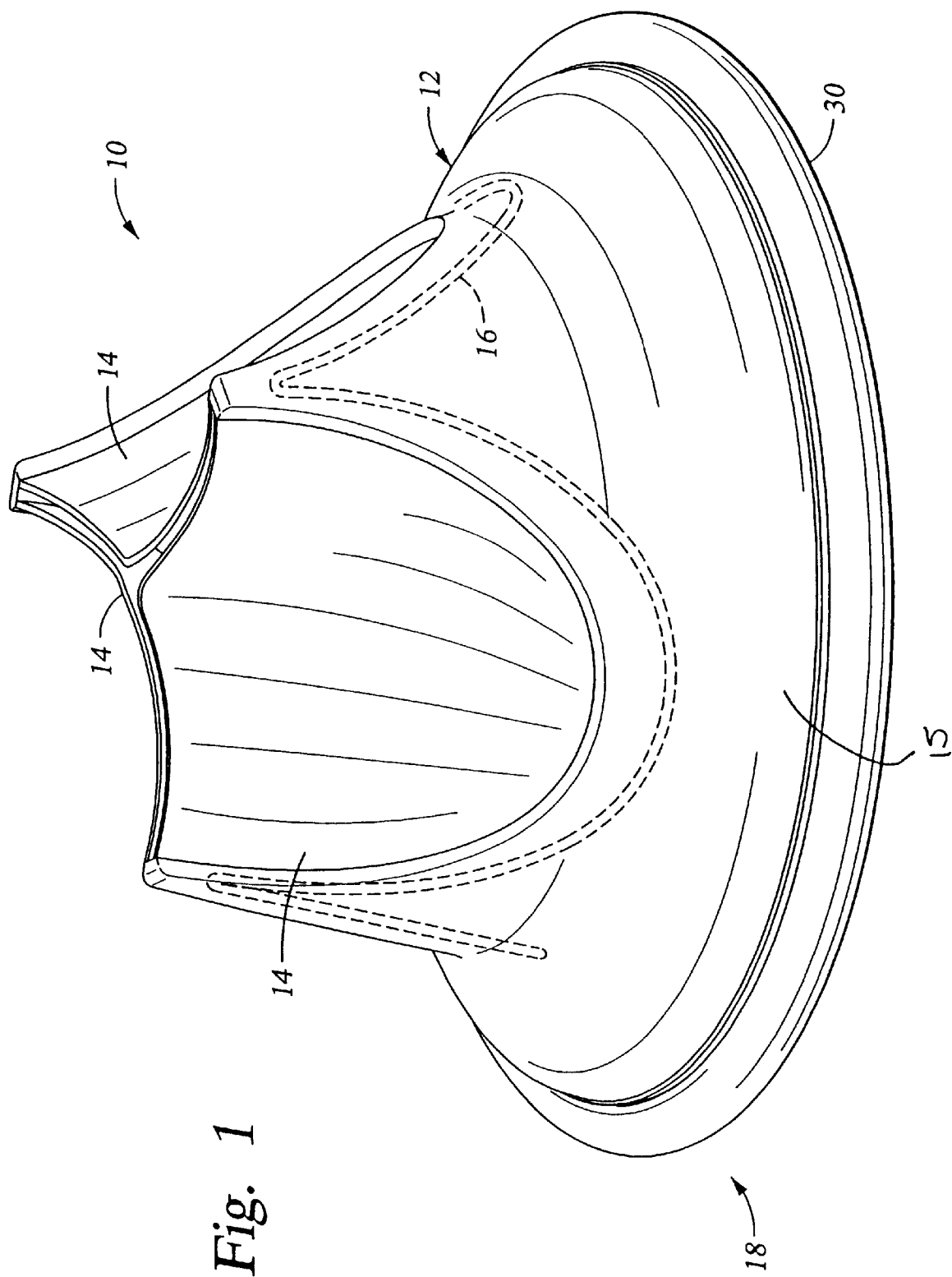
FIG. 1 is a perspective view of a heart valve having a cuff assembly attached thereto.

FIG. 1 is a perspective view of a tri-leaflet prosthetic heart valve 10 having an annular valve body 12 and three flexible leaflets 14 made of a bio-compatible polymer such as silicone or polyurethane. A stent 16, made of metal or plastic, is disposed in or otherwise coupled to the valve body 12 for reinforcement. A sewing cuff assembly 18 is coupled to the base of the valve body 12. The sewing cuff assembly allows a surgeon to suture the prosthetic heart valve 10 to the natural heart.

FIG. 2 is a partial cross sectional view of a heart valve 10 illustrating one embodiment of a sewing cuff assembly 18. The valve body 12 includes a base portion 15 having a periphery 20 defining a radius RP. In the embodiment of FIG. 2, the radius RP is defined by the outer radius of stiffening ring 26. The periphery 20 of valve body 12 comprises a groove 22 defining a radius RG for receiving a pair of lock rings 24, 25 for securing the sewing cuff assembly 18 to the valve body 12.

Lock rings 24, 25 preferably have the same radius RL. In preferred embodiments, the radius RL of the lock rings is less than the radius RP of the valve periphery 20. This ensures that the rings 24, 25 are securely held in groove 22. In an even more preferred embodiment, the radius RL of the lock rings 24, 25 is also greater than the radius RG of groove 22. This further ensures that, when located within groove 22, rings 24, 25 do not place stress on the periphery 20 of valve body 12. The groove 22 may also comprise a stiffening ring 26. The stiffening ring 26 is disposed in the groove 22 and coupled to or otherwise secured to the heart valve by molding, press fitting the component into place, or other fabrication techniques known in the art., e.g. adhesives.

The stiffening ring 26 can be made of biocompatable material such as cobalt chromium or titanium and provides a rigid channel 28 in which the lock rings 24, 25 can be received to secure the sewing cuff assembly 18 to the valve body 12. The stiffening ring can be a continuous ring or can be discontinuous. In another embodiment (not shown) the stiffening ring can form a lower portion of a stent in the valve body. In this configuration, the stent may be formed with a groove in its lower portion defining a channel to receive the lock rings 24, 25. U.S. Pat. Nos. 5,397,346 and 5,397,348 disclose exemplary methods of incorporating stiffening rings into a prosthetic heart valve.

The embodiment of the suture cuff assembly 18 shown in FIG. 2 includes two lock rings 24, 25 having an outer covering 30 coupled thereto. The outer covering can be polyester, Teflon felt or Dacron. The lock rings 24, 25 are preferably continuous rings made from a biocompatible material such as titanium. The lock rings 24, 25 can have a circular, square (as shown in FIG. 2), rectangular or other geometric cross section. The outer covering 30 is attached to the lock rings with stitches 32, 34. In the embodiment of FIG. 2, each end of the outer covering 30 is wrapped around a lock ring 24, 25 and then stitched, thereby enclosing the lock ring in the suture material. Other methods of coupling the suture material to the lock rings, such as stapling, will be apparent to persons of skill in the art.

A filler material 36 can optionally be placed within an interior of the outer covering 30 defined when the suture material is stitched around the lock rings 24, 25. Filler material can include Teflon felt or Dacron, for example. The filler material 36 provides rigidity and reinforcement to the outer covering 30 on implantation into a heart. The sewing cuff assembly 18, including both the outer covering 30 and the filler material 36, if used, also help prevent perivalvular leakage around valve 10 when the valve is closed.

A suture cuff assembly can be assembled and coupled to a heart valve as follows. The pair of lock rings 24, 25 are positioned inside opposing ends of the cloth tube, such as a polyester tube, and sutured, stapled or otherwise secured in place. An optional filler material 36 can be positioned adjacent the outer covering 30 and enclosed between the two lock rings 24, 25. A stiffening ring 26, such as a U-shaped ring as illustrated in FIG. 2, is coupled to channel 28 and groove 22 in heart valve periphery 20. The lock-rings 24, 25 are then snapped fit around the stiffening ring 26 into channel 28 (and groove 22) in valve body 12. The lock rings 24, 25 are made of a material, such as titanium, which enables the lock rings 24, 25 to be positioned in the groove 22 in much the same way as a clincher bicycle tire is fitted onto a bicycle rim.

Channel 28, stiffening ring 26, and groove 22 prevent both vertical and lateral displacement of the suture cuff assembly 18 while enabling rotation of the lock rings 24, 25 (and thus sewing cuff assembly 18) relative to valve body 12. The assembled heart valve can then be sutured into the annulus of a patient's heart after the native valve is removed. This configuration of a suture cuff assembly enables rapid fabrication of a heart valve with minimal contact with the valve body. In addition, this configuration eliminates the need for sutures or pins to secure the sewing cuff to the valve body.

Another embodiment of the heart valve of the present invention is depicted partial cross sectional view in FIG. 3. The heart valve comprises a single lock ring 24 secured in groove 22. More particular, the lock ring 24 is placed in a channel 28 of a stiffening ring 26, which in turn is disposed within groove 22 of valve periphery 20. One end of outer covering 30 is wrapped around the lock ring 24 and stitched together by representative suture 38 to secure the outer covering to the lock ring 24. The outer material 30 is then folded back on itself and stitched together at opposing ends 40, 42 by stitching, such as by representative suture 44.

As shown in the embodiment of FIG. 3, the material is preferably folded back and stitched together at a location adjacent the lock ring 24. This configuration of the suture material provides a sufficient amount and thickness of suture material 30 to enable the suture material to be reliably secured in a heart and to fill any space between the valve body and a heart annulus in which the valve is positioned. In the embodiment shown in FIG. 3, the material is folded back on itself to provide a sewing cuff which is four layers thick. While the embodiment shown has the material folded on itself to provide four layers of material adequate for attachment, more or few layers could be used as well. In addition, filler material such as filler material 36 depicted in FIG. 2 could also be used in single lock ring embodiments if desired.

The stiffening ring into which the lock ring is secured on assembly can have a lower vertical height than the two lock ring embodiment. The vertical height is a consideration in the application or position the valve is to be inserted. For example, in the aortic position, surgeons prefer to use a smaller valve. Therefore, a valve having a reduced or minimized height may be provided by a single lock ring embodiment.

The shape, configuration and materials used for the lock ring 24, the stiffening ring 26 and the outer covering 30 are the same or similar to those described above in reference to the two lock ring embodiment.

Each of the embodiments described above provide for rotation of the valve body 12 within the sewing cuff assembly 18 for ease of positioning following placement within a heart. For example, in the mitral position, the valve is positioned by the surgeon without the benefit of line of sight access. After placement, the surgeon can manipulate the rotational position of the valve to ensure proper positioning and subsequent operation of the replacement valve. The frictional force between the sewing cuff and the valve body is sufficient to prevent rotation therebetween unless manipulated by the surgeon so that the position of the valve is maintained after proper positioning.

Figure 4:
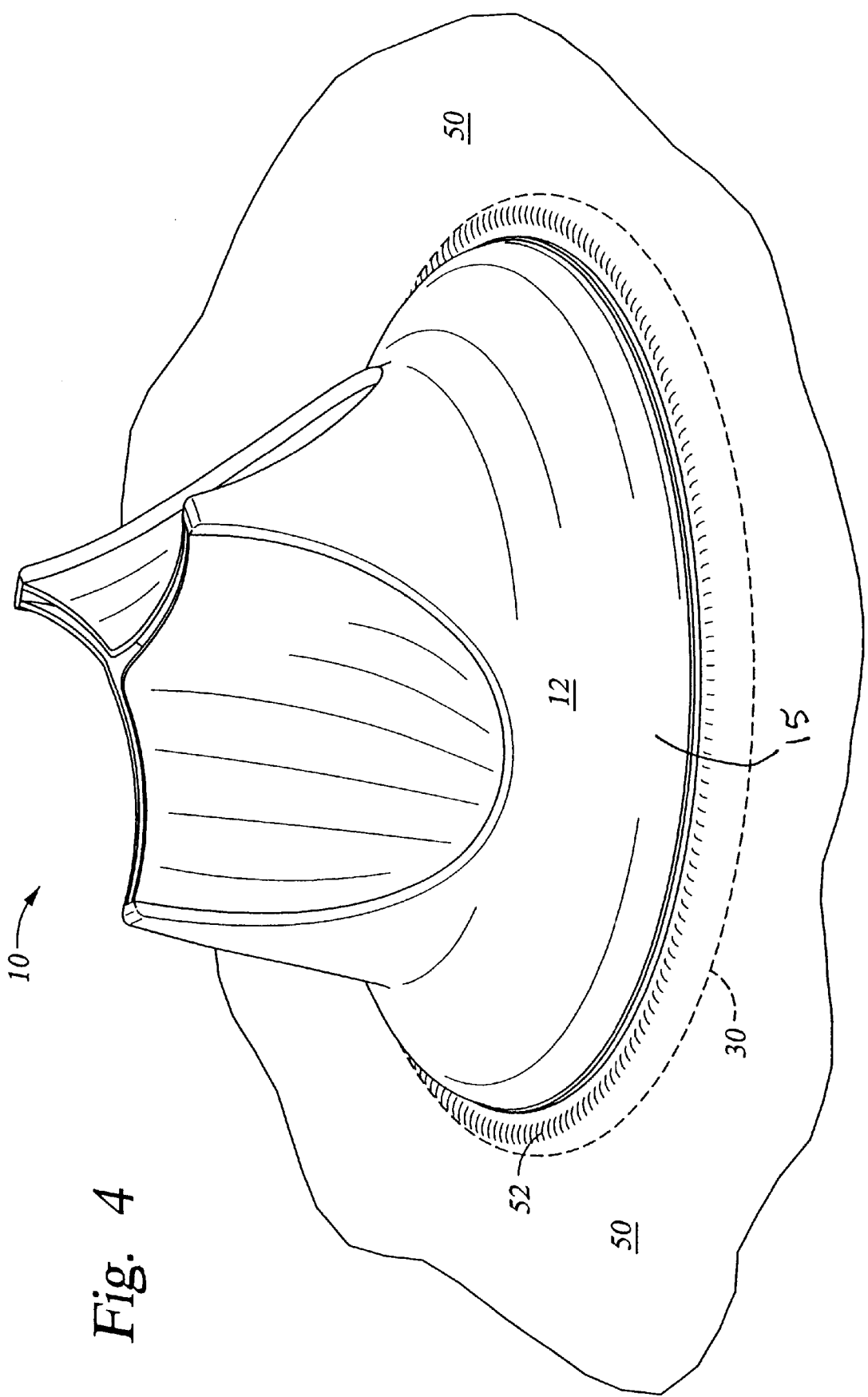
FIG. 4 a perspective view of a heart valve sewn into an annulus of a heart.

FIG. 4 is a perspective view of a prosthetic heart valve 10 attached to the natural heart tissue, e.g., annulus 50, of a patient. The heart valve is sewn into place by suturing the annulus tissue to the sewing cuff 18 by stitches 52. The lock ring(s) secure the suture material to the valve body 12 and the assembly provides attachment of the prosthetic heart valve in a patient's heart.

While foregoing is directed to the preferred embodiment of the present invention, other and further embodiments of the invention may be devised without departing from the basic scope thereof, and the scope thereof is determined by the claims that follow.

What is claimed is:

1. A heart valve, comprising:
   (a) a valve body comprising a base having an outer periphery, said outer periphery comprising a groove, wherein the base of the valve body comprises a stiffening ring and the groove is at least partially in the stiffening ring; and
   (b) a suture cuff assembly comprising at least one lock ring, a suture material coupled to the lock ring, and a filler material disposed inside at least a portion of the suture material, wherein the lock ring is positioned within the groove.

2. The heart valve of claim 1 wherein the stiffening ring is formed integrally in the valve body.

3. The heart valve of claim 1 wherein the stiffening ring comprises a U-shaped channel.

4. The heart valve of claim 1 wherein the stiffening ring comprises a portion of a scent coupled to the valve body.

5. The heart valve of claim 1 wherein the stiffening ring is discontinuous.

6. A heart valve, comprising:
   (a) a valve body comprising a base having an outer periphery, said outer periphery comprising a groove, wherein the valve body comprises a material selected from the group consisting of polyurethane, silicone and combinations thereof; and
   (b) a suture cuff assembly comprising at least one lock ring and a suture material coupled to the lock ring, said lock ring is positioned within said groove.

7. A heart valve, comprising:
   (a) a valve body comprising a flow orifice and a base comprising an outer periphery having a first radius, said outer periphery comprising a groove having a second radius less than said first radius; and
   (b) a suture cuff assembly comprising:
      (i) at least one lack ring having a third radius, said third radius being greater than said second radius and less than said first radius; and
      (ii) a sewing cuff material disposed at least partially around and coupled to said at least one lock ring;
   wherein the at least one lock ring is positioned within said groove.

8. A heart valve, comprising:
   (a) a valve body,
   (b) a stent coupled to the valve body, wherein the stent comprises a lower portion comprising a groove; and
   (c) a suture cuff assembly comprising:
      (i) a, least one lock ring; and
      (ii) a suture material disposed at least partially around and secured to the lock ring;
   wherein said at least one lock ring is positioned within said groove.

9. The heart valve of claim 8 wherein the suture cuff assembly further comprises a filler material disposed inside at least a portion of the suture material.

10. The heart valve of claim 8 further comprising a stiffening ring that comprises the groove for receiving the at least one lock ring.

11. The heart valve of claim 8 wherein the suture material comprises first and second ends, said end being coupled to said at least one lock ring.

12. A heart valve, comprising:
   (a) a valve body having an outer circumferential rim;
   (b) a suture cuff assembly comprising:
      (i) at least one lock ring; and
      (ii) a material disposed at least partially around and secured to the lock ring; and
   (c) a stiffening ring coupled to the valve body and defining a lock ring receiving channel at least partially therein;
   wherein stiffening ring comprises a portion of a stent coupled to the valve body.

13. The heart valve of claim 12 wherein the suture cuff assembly further comprises a filler material disposed inside at least a portion of the suture material.

14. The heart valve of claim 12 further comprising at least two lock rings and wherein the suture material is secured to each lock ring.

15. The heart valve of claim 12 wherein the suture material is disposed around the lock ring on at least one first end thereof and a second opposing end is secured to the first end disposed around the lock ring.

16. The heart valve of claim 12 wherein the stiffening ring U-shaped channel.

17. A heart valve, comprising:
   (a) a valve body having an outer circumferential rim;
   (b) a suture cuff assembly comprising:
      (i) at least one lock ring; and
      (ii) a suture material disposed at least partially around and secured to the lock ring; and
   (c) a stiffening ring coupled to the valve body and defining a lock ring receiving channel at least partially therein;
   wherein the stiffening ring is discontinuous around the perimeter of the valve body.

18. The heart valve at claim 17 wherein the suture cuff assembly further comprises a filler material disposed inside at least a portion of the suture material.

19. The heart valve of claim 17 further comprising at least two lock rings and wherein the suture material is secured to each lock ring.

20. The heart valve of claim 17 wherein the suture material is disposed around the lock ring on at least one first end thereof and a second opposing end is secured to the first end disposed around the lock ring.

21. The bean valve of claim 17 wherein the stiffening ring comprises a U-shaped channel.

22. The heart valve of claim 17 wherein the stiffening ring is formed integrally into the valve body.

23. The heart valve of claim 17 wherein the stiffening ring comprises a portion of a stent coupled to the valve body.

* * * * *

UNITED STATES PATENT AND TRADEMARK OFFICE
CERTIFICATE OF CORRECTION

PATENT NO.    : 6,716,244 B2
DATED         : April 6, 2004
INVENTOR(S)   : Tammi Klaco It is certified that error appears in the above-identified patent and that said Letters Patent is hereby corrected as shown below:

<u>Column 6,</u>
Line 2, delete "a," and insert -- at -- therefor.
Line 14, delete "said end" and insert -- said first end -- therefor.
Line 24, delete "wherein stiffening" and insert -- wherein the stiffening -- therefor.
Line 37, after "ring", and insert -- comprises a --.
Line 60, delete "bean" and insert -- heart -- therefor.

Signed and Sealed this

Eighth Day of June, 2004

JON W. DUDAS
*Acting Director of the United States Patent and Trademark Office*

UNITED STATES PATENT AND TRADEMARK OFFICE
Certificate

Patent No. 6,716,244 B2                                                                           Patented: April 6, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Tammi Klaco, Austin, TX (US); and Riyad Moe, Huntsville, TX (US).

Signed and Sealed this Fourth Day of September 2007.

CORRINE M. MCDERMOTT
*Supervisory Patent Examiner*
Art Unit 3738